United States Patent [19]
Wildemeersch

[11] Patent Number: 5,303,717
[45] Date of Patent: Apr. 19, 1994

[54] DEVICE FOR FIXING A CONTRACEPTIVE DEVICE TO THE WALL OF THE UTERUS

[76] Inventor: Dirk Wildemeersch, Vossenhul 8, Knokke-Heist, B-8300, Belgium

[21] Appl. No.: 777,365
[22] PCT Filed: Jul. 3, 1990
[86] PCT No.: PCT/BE90/00038
§ 371 Date: Nov. 22, 1991
§ 102(e) Date: Nov. 22, 1991
[87] PCT Pub. No.: WO91/00714
PCT Pub. Date: Jan. 24, 1991

[30] Foreign Application Priority Data
Jul. 12, 1989 [BE] Belgium ................ 8900760

[51] Int. Cl.⁵ ............................ A61F 6/06
[52] U.S. Cl. ...................... 128/830; 128/840
[58] Field of Search ................ 128/830–841

[56] References Cited

U.S. PATENT DOCUMENTS

| | | | |
|---|---|---|---|
| 3,598,115 | 8/1971 | Horne | 128/833 |
| 3,659,596 | 5/1972 | Robinson | 128/833 |
| 3,854,475 | 12/1974 | Bucalo | 128/833 |
| 3,888,975 | 6/1975 | Ramwell | 424/15 |
| 3,954,103 | 5/1976 | Garcia-Roel | 128/839 |
| 3,993,057 | 11/1976 | Ramwell | 128/833 |
| 4,034,749 | 7/1977 | Von Kesseru | 128/833 |
| 4,111,196 | 9/1978 | Emmett | 128/833 |
| 4,326,511 | 4/1982 | Zimerman | 128/833 |
| 4,708,134 | 11/1987 | Wildemeersch | 128/840 |
| 4,721,105 | 1/1988 | Wildemeersch | 128/840 |
| 4,807,610 | 2/1989 | Gainutdinova | 128/833 |

FOREIGN PATENT DOCUMENTS 899286 10/1984 Belgium.

Primary Examiner—Michael A. Brown
Attorney, Agent, or Firm—Weingarten, Schurgin, Gagnebin & Hayes

[57] ABSTRACT

A device for fixing a contraceptive device to the wall of the uterus is disclosed. The fixing device consists of a thread (10) of non-biodegradable material, designed to be attached to the contraceptive device, and a retaining member (11) implantable in the tissue of the uterus; this retaining member (11) consists of a permanent element (12) of non-biodegradable material and a temporary element (13) of biodegradable material which temporarily confers on the retaining member (11) a greater resistance to pulling out than that of the permanent element (12) alone. The device according to the invention is to be used during the period immediately following confinement.

8 Claims, 1 Drawing Sheet

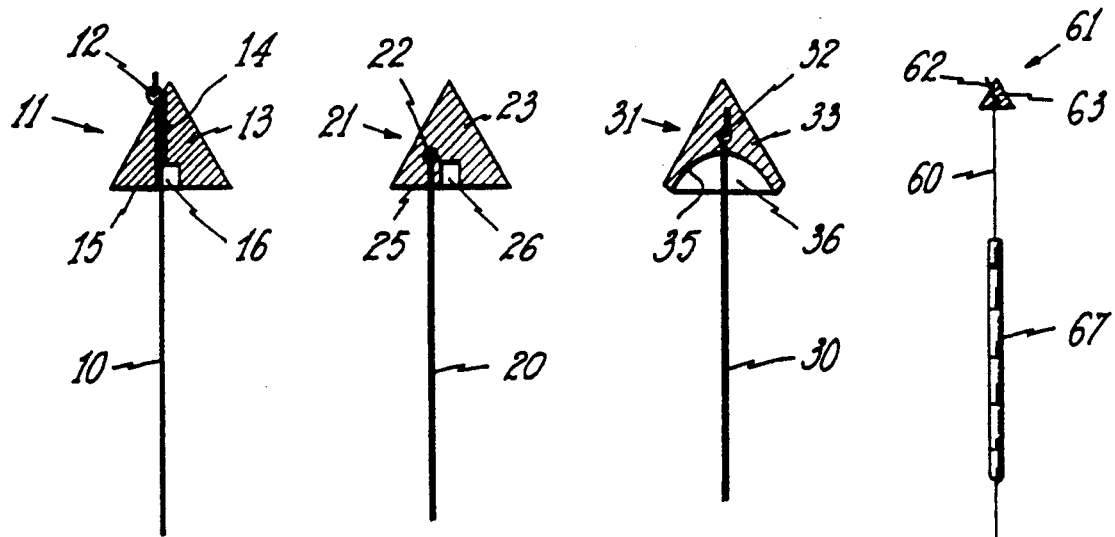
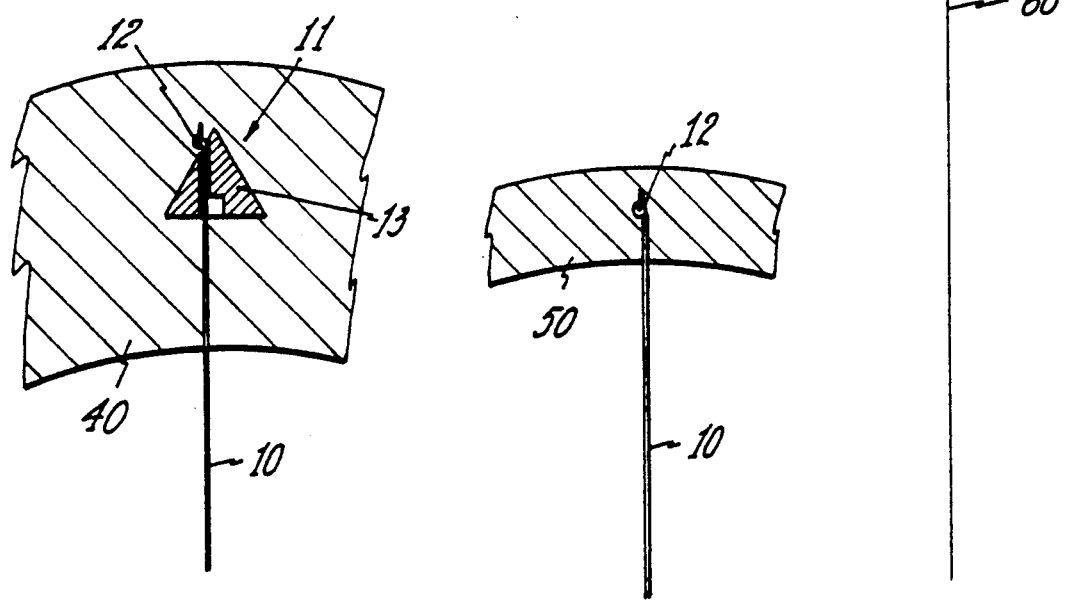

DEVICE FOR FIXING A CONTRACEPTIVE DEVICE TO THE WALL OF THE UTERUS

FIELD OF THE INVENTION

The present invention has as its subject matter a device for fixing a contraceptive device to the wall of the uterus, of the type consisting of a thread, integral with the contraceptive device, and a retaining member implantable in the tissue of the uterus and integral with the thread.

BACKGROUND OF THE INVENTION

Interest in contraceptive devices fixed to the wall of uterus appeared first of all in the field of positioning I.U.D.s during the period immediately subsequent to confinement or post-partum period. Intrauterine contraception is in fact considered by the experts as an effective, cheap and temporary means of contraception, temporary being meant in the sense that, once the intra-uterine device is withdrawn, pregnancies are again possible. Moreover, the post-partum period is considered to be a strategically important period for the insertion of an intra-uterine device, this being particularly true in countries where women have relatively little contact with medical services. In effect, at the time of confinement, the motivation to use contraceptive devices is great; moreover, at that moment the insertion of a contraceptive device is easy, painless, does not cause additional bleeding and can be untertaken by the nurse or midwife. Another advantage, if insertion of the intra-uterine device is undertaken immediately after confinement, is that the patient remains under medical supervision for at least several hours after insertion. Furthermore, positioning of an intra-uterine device does not interfere with breastfeeding, and nor does it require the intervention of medical personnel other than those already involved in the confinement However, immediately after confinement, the dimensions of the uterine cavity and the neck of the womb are large, a fact which entails significant risks of rejection and/or displacement of the intra-uterine device.

This is one of the reasons which have led to the designing of intra-uterine devices fixed to the wall of the uterus. Such devices have been described in particular in US-A-3 954 103 and BE-A-899 286.

Another reason for fixing the intra-uterine device to the wall of the uterus is that this method permits the use of highly deformable intra-uterine devices which, without this fixing, would be expelled from the uterus. In fact, a highly deformable intra-uterine device is better tolerated in the uterus, and runs less risk of causing damage to the wall of the uterus, than a device held in the uterus by its shape. Such devices have been described in particular in EU-A-0100924 and BE-A-901 652.

Various retaining members, implantable in the wall of the uterus, have been described in these prior documents.

As stated above, an intra-uterine contraceptive device has the advantage of being a temporary device, that is to say, capable of being removed. If it is wished to keep this advantage when contraceptive devices are used which are fixed to the wall of the uterus, it is thus also necessary to be able to release the fixture from the wall of the uterus. If, at the time of insertion and fixing of the intra-uterine device to the wall of the uterus, use is necessarily made of a device for introducing and fixing the contraceptive device, it would seem impossible to have to use a device to release the fixture, which can as a rule only be effected by drawing and pulling. Insofar as this is the case, it would seem difficult to remove the retaining member implantable in the tissue of the uterus described in EU-A-0100924 from the tissue of the uterus without causing considerable damage thereto. The same is true of the pulling-out of the point shown in US-A-3954103 and nevertheless advocated in this Patent.

This is the reason why, in its prior Patents BE-A-899 286 and BE-A-901 652, the Applicant principally envisages, as the retaining member implantable in the tissue of the uterus, a small deformation of the thread, especially such as a knot formed in the thread.

In effect, such an implantable retaining member has the advantage, first of all, of achieving suitable fixing to the tissue of the uterus, at least outside the post-partum period, and, moreover, of enabling releasing of the fixture, by pulling, without damaging the wall of the uterus.

However, experience has shown that a small deformation of a form suitable for preventing damage to the wall of the uterus at the time of withdrawal, such as knot in the thread, may be insufficient to ensure satisfactory anchorage in the tissue of a uterus during the immediate post-partum period The tissue of a dilated uterus, immediately after confinement, is, in fact, much less firm than the tissue of a uterus in the normal state.

SUMMARY OF THE INVENTION

The present invention consequently has as its subject matter a device for fixing a contraceptive device to the wall of the uterus, enabling satisfactory fixing during the immediate post-partum period, and being capable of release by pulling from the uterus returned to the normal state without causing damage to the tissue of the uterus.

This aim is achieved with a device for fixing a contraceptive device to the wall of the uterus consisting of a thread of non-biodegradable material designed to be attached to the contraceptive device and a retaining member implantable in the tissue of the uterus and integral with the thread, the retaining member implantable in the tissue of the uterus consisting of a permanent element, of non-biodegradable material, and a temporary element, of biodegradable material temporarily conferring to the implantable retaining member a greater resistance to pulling out than that provided by the permanent element alone.

According to another characteristic of the invention, the temporary element, of biodegradable material, of the implantable retaining member, is pierced with a channel through which the thread passes and is held on the thread by the permanent element, of non-biodegradable material, of the implantable retaining member.

According to another characteristic of the invention, the permanent element, of non-biodegradable material, is buried in the temporary element, of biodegradable material, of the implantable retaining member.

According to yet another characteristic of the invention, the retaining member implantable in the tissue of the uterus is generally pointed in form, to facilitate its penetration into the tissue of the uterus.

According to another characteristic of the invention, the element of biodegradable material of the retaining member implantable in the tissue of the uterus constitutes the major part of the volume of the implantable retaining member, is in the form of a point and is pierced by a channel opening in the upper part of the point through which the thread passes, and a deformation in the thread, constituting the permanent element of the implantable retaining member and formed beyond the channel at the opposite end of the thread from the contraceptive device, also ensures that the element of biodegradable material is held on the thread.

According to another characteristic of the invention, the deformation in the thread, constituting the permanent element of the implantable retaining member, is smaller in volume and of a form suitable to allow its withdrawal, under the effect of sufficient pulling, from the tissue of the uterus without damaging the latter.

According to a preferred embodiment of the invention, the deformation of the thread, constituting the permanent element of the implantable retaining member, is a knot in the thread.

According to one characteristic of the invention, the temporary element of biodegradable material of the implantable retaining member comprises, in the area thereof remote from the point, means for receiving the end of a needle, with a view to its implantation in the wall of the uterus.

BRIEF DESCRIPTION OF THE DRAWINGS

The invention will be better understood with reference the description, as well as to the attached drawings, which show, purely by way of example, various embodiments of the invention and in which:

FIGS. 1 to 3 show, in section, various embodiments of the device for fixing an intra-uterine contraceptive device according to the invention to the wall of the uterus;

FIGS. 4 and 5 show, also in section, a device according to the invention in place in the wall of the uterus, respectively as i appears immediately after its introduction into the wall of the uterus during the immediate post-partum period, and some months later when the uterus has returned to its normal state;

FIG. 6 is a complete view of the assembly consisting of the intra-uterine device, the device for fixing it to the wall of the uterus and the device for the extraction thereof.

DESCRIPTION OF THE PREFERRED EMBODIMENT(s)

With reference to the drawings, and more especially to the embodiments shown in FIGS. 1 and 3, the device for fixing a contraceptive device to the wall of the uterus comprises, according to the invention, a thread 10;20;30 of non-biodegradable material, and a retaining member 11;21;31 implantable in the tissue of the uterus, integral with the thread 10;20;30. The retaining member 11,21,31 consists of a permanent element 12;22;32, of non-biodegradable material, and a temporary element 13;23;33 of biodegradable material. To facilitate its penetration into the tissue of the uterus, the temporary element 13;23;33 has the general shape of a point, and has dimensions, at its base, considerably greater than those of the permanent element 12;22;32, thus conferring to the retaining member 11;21;31 a considerably greater resistance to pulling out than that of the permanent element 12;22;32.

In the embodiment of FIG. 1, the permanent element 12 of the retaining member 11 is a knot, formed in the thread 10 after passage of the latter through a channel 14 pierced in the temporary element 13.

In the embodiment of FIG. 2 the permanent element 22 of the retaining member 21 is an attached piece, generally spherical in form, fixed to the thread by welding/adhesion, the whole of the end of the thread and the permanent element 22 being buried in the temporary element 23.

Finally, in the embodiment of FIG. 3, the permanent element 32 of the retaining member 31 is a knot in the thread 30, buried in the temporary element 33.

For its insertion into the tissue of the uterus with the aid of a needle device of known type, for example of the type represented by those described and shown in Patents BE-A-899 286 or BE-A-901 562, the base 15;25;35 of the temporary element 13;23;33 comprises means for cooperating with a needle. These cooperation means are as follows: in the embodiment of FIG. 1, a broadening 16 of the channel 14 from the base 15 of the temporary element 13; in the embodiment of FIG. 2, a recess 26 formed in the base 25, and finally in the embodiment of FIG. 3 a hollow 36 consisting of the concave form of the base 35.

Use of the device is shown in FIGS. 4 and 5, which show a device of the type shown in FIG. 1, FIG. 4 showing it as it appears at the time of implantation into the tissue of the uterus during the immediate post-partum period and FIG. 5 showing it as it appears some months later in the tissue of the uterus after it has returned to its normal condition.

In FIG. 4, the wall 40 of the uterus in the immediate post-partum period is thick and consists of tissue of low strength. At this time, the implanted retaining member 11, consisting of the permanent element 12 of non-biodegradable material and the temporary element 13 of biodegradable material, has essentially the size and form of the temporary element 13 of biodegradable material, and this ensures very strong anchorage in the wall 40 of the uterus.

FIG. 5 shows the anchorage as it appears several months after the implantation shown in FIG. 4. At this time, the wall 50 of the uterus has diminished considerably in thickness, while the tissue of which it consists has gained in mechanical strength Over the same time, the temporary element 13 of the implanted retaining member 11 has dissolved and disappeared leaving only the permanent element 12. This latter, given the consistency of the uterine tissue, ensures entirely satisfactory anchoring of the thread 10 in the uterine tissue. However, it can, with sufficient traction exerted on the thread 10, be extracted by pulling from the uterine tissue. Given the reduced size and generally substantially spherical shape of the permanent element 12, this extraction by pulling may be undertaken without causing damage to the tissue of the wall 50 of the uterus.

Finally, with reference to FIG. 6, which shows a preferred embodiment of the invention, an intra-uterine contraceptive device comprises, according to the invention, a device for fixing it to the wall of the uterus consisting of a thread 60 and a retaining member 61 implantable in the tissue of the uterus, this retaining element 61 itself consisting of a permanent element 62 of non-biodegradable material, and a temporary element 63 of biodegradable material. According to this embodiment, this permanent element 62 consists of a knot in the end of the thread 60 beyond the temporary element 63, while the thread 60 continues below the temporary element 63, to receive a contraceptive device 67 proper, and while this same thread 60 continues below the contraceptive device 67, to constitute an extraction device 68.

I claim:

1. A device for fixing a contraceptive device to the wall of a uterus, said device consisting of:
   a thread of non-biodegradable material, designed to be attached to the contraceptive device, and
   a retaining member implantable in the wall of the uterus and integral with the thread, characterized in that the retaining member implantable in the wall of the uterus consists of a permanent element, of now-biodegradable material, and a temporary element, of biodegradable material, the temporary element, of biodegradable material, the temporary element temporarily conferring to the implantable retaining member greater resistance to pulling out of the uterine wall than that of the permanent element alone.

2. A device according to claim 1, characterized in that the temporary element, of biodegradable material, of the implantable retaining member is held on the thread by the permanent element, of non-biodegradable material, of the implantable retaining member.

3. A device according to claim 1, characterized in that the permanent element, of non-biodegradable material, is buried in the temporary element, of biodegradable material, of the implantable retaining member.

4. A device according to claim 1, characterized in that the retaining member implantable in the tissue of the uterus, is generally pointed to form to facilitate its penetration into the wall of the uterus.

5. A device according to claim 1, characterized in that the element of biodegradable material of the retaining member implantable in the wall of the uterus constitutes the major part of the size of the implantable retaining member, is pointed in shape and is pierced by a channel opening in the upper part of the point through which the thread passes, and in that a deformation in the thread, constituting the permanent element of the implantable retaining member and formed beyond the channel at the opposite end of the thread from the contraceptive device, also ensures that the element of biodegradable material is held on the thread.

6. A device according to claim 1, characterized in that the deformation in the thread, constituting the permanent element of the implantable retaining member, is smaller in volume and of generally spherical form to allow its withdrawal, under the effect of sufficient pulling, from the wall of the uterus without damaging the latter.

7. A device according to claim 6, characterized in that the deformation in the thread, constituting the permanent element of the implantable retaining member, is a knot in the thread.

8. A device according to any one of claims 1, 2, 3, 4, 5, 6, or 7, characterized in that the temporary element of biodegradable material of the implantable retaining member comprises, in the area thereof remote from the point, means for receiving the end of a needle, with a view to its implantation in the wall of the uterus.

* * * * *

UNITED STATES PATENT AND TRADEMARK OFFICE
CERTIFICATE OF CORRECTION

PATENT NO. : 5,303,717
DATED : April 19, 1994
INVENTOR(S) : Dirk Wildemeersch

It is certified that error appears in the above-indentified patent and that said Letters Patent is hereby corrected as shown below:

Column 1, line 15, "uterus appeared" should read --the uterus appeared--.

Column 1, line 38, "confinement" should read --confinement.--, ending the sentence with a period.

Column 2, line 27, "period The" should read --period. The--, (with a period between the sentences).

Column 3, line 29/30, "reference the" should read --reference to the--.

Column 3, line 39, "as i appears" should read --as it appears--.

Column 4, line 44, "strength Over" should read --strength. Over--, (with a period between the sentences).

Column 5, line 13, "now-biodegradable" should read --non-biodegradable--.

UNITED STATES PATENT AND TRADEMARK OFFICE
CERTIFICATE OF CORRECTION

PATENT NO. : 5,303,717
DATED : April 19, 1994
INVENTOR(S) : Dirk Wildemeersch

It is certified that error appears in the above-indentified patent and that said Letters Patent is hereby corrected as shown below:

Column 5, line 15/16, "element, of biodegradable material, the temporary" appears twice, please delete the first occurrence.

Signed and Sealed this

Eighteenth Day of October, 1994

Attest:

BRUCE LEHMAN

Attesting Officer

Commissioner of Patents and Trademarks